United States Patent [19]

Verge et al.

[11] 4,035,390

[45] July 12, 1977

[54] THIAZOLE DERIVATIVES

[75] Inventors: John Pomfret Verge, Henley-on-Thames; Martin Charles Neville, Tadley, both of England

[73] Assignee: Lilly Industries, Ltd., London, England

[21] Appl. No.: 713,009

[22] Filed: Aug. 9, 1976

Related U.S. Application Data

[60] Division of Ser. No. 542,989, Jan. 22, 1975, Pat. No. 3,989,690, which is a continuation-in-part of Ser. No. 398,726, Sept. 19, 1973, abandoned, which is a continuation-in-part of Ser. No. 259,186, June 7, 1972, abandoned.

[30] Foreign Application Priority Data

June 19, 1971 United Kingdom ............. 28882/71

[51] Int. Cl.$^2$ ...................................... C07D 417/00
[52] U.S. Cl. ............................................ 260/302 H
[58] Field of Search ................................. 260/302 H

[56] References Cited

U.S. PATENT DOCUMENTS

| 3,691,178 | 9/1972 | Baldwin et al. ................ 260/302 H |
| 3,794,658 | 2/1974 | Carter et al. ................... 260/302 H |
| 3,984,426 | 10/1976 | Winkelmann et al. ........ 260/302 H |

*Primary Examiner*—R. Gallagher
*Attorney, Agent, or Firm*—Kathleen R. S. Page; Everet F. Smith

[57] ABSTRACT

2-Nitroimidazolyl-4-thiomorpholinoiminoalkyl thiazoles are useful as anti-parasitic agents, being active against Trypanosomidae, and may be prepared by reaction of novel 2-nitroimidazolyl-4-acylthiazoles with an N-aminothiomorpholine.

6 Claims, No Drawings

THIAZOLE DERIVATIVES

CROSS-REFERENCE TO RELATED APPLICATIONS

This is a division of our copending application Ser. No. 542,989, filed Jan. 22, 1975, and issued Nov. 2, 1976 as U.S. Pat. No. 3,989,690. Application Ser. No. 542,989 was a continuation-in-part of our then copending application Ser. No. 398,726, filed Sept. 19, 1973, and abandoned after the filing of application Ser. No. 542,989. Application Ser. No. 398,726 was a continuation-in-part of our then copending application Ser. No. 259,186, filed June 7, 1972, and abandoned after the filing of application Ser. No. 398,726.

BRIEF SUMMARY OF THE INVENTION

This invention relates to certain thiazole derivatives of use in the treatment of parasitic infections of humans and animals. More especially, the invention is concerned with compounds which are 2-substituted-4-(1'-thiomorpholinoiminoalkyl) thiazoles, a process for their preparation, pharmaceutical compositions containing them and a method of treating a patient suffering from a parasitic infection involving the use of said compounds and compositions.

DETAILED DESCRIPTION

According to the present invention therefore, there are provided thiazole derivatives of the formula:

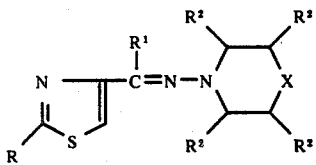

wherein X represents S, S=O or

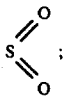

$R^1$ represents hydrogen or $C_{1-4}$ alkyl; each $R^2$ independently represents hydrogen or $C_{1-4}$ alkyl; and R represents a 1-($R^3$-substituted)-5-nitroimidazol-2-yl group in which $R^3$ represents $C_{1-4}$ alkyl or $C_{2-4}$ alk-1-enyl.

Compounds of formula I in which $R^1$ is hydrogen ar preferred.

The term "alkyl" is used herein to mean a straight or branched chain saturated hydrocarbon group whilst the prefix "$C_{1-4}$" or "$C_{2-4}$" applied thereto or to any other group means that the group in question contains from 1 to 4 or 2 to 4 carbon atoms respectively. Exemplary of such alkyl groups are methyl, ethyl, isopropyl, n-butyl, s-butyl and t-butyl. The term "alk-1-enyl" is used to mean a straight or branched chain hydrocarbon group containing a single double bond linking the first and second carbons in the chain, examples of which are vinyl, prop-1-enyl, isopropenyl, but-1-enyl, and isobutenyl.

Within the above-defined compounds of formula I, a further preferred group are those where $R^1$ is hydrogen, methyl or ethyl; two of the $R^2$ groups represent hydrogen and the other $R^2$ groups independently represent hydrogen, methyl or ethyl; and $R^3$ represents methyl, ethyl, or vinyl. Most advantageously, X is

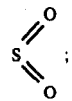

$R^1$ is hydrogen or methyl; three of the $R^2$ groups are hydrogen and the remaining $R^2$ group is hydrogen or methyl; and $R^3$ is methyl or vinyl.

As examples of compounds falling within the above preferred group, there may be named 2-(1-methyl-5-nitroimidazol-2-yl)-4-(thiomorpholinoimino-methyl)thiazole
2-(1-methyl-5-nitroimidazol-2-yl)-4-[1-(thiomorpholinoimino)-ethyl]thiazole
2-(1-methyl-5-nitroimidazol-2-yl)-4-(thiomorpholinoiminomethyl)-thiazole-1'-oxide
2-(1-sec-butyl-5-nitroimidazol-2-yl)-4-(thiomorpholinoimino-methyl)thiazole
2-(1-methyl-5-nitroimidazol-2-yl)-4-[1-(thiomorpholinoimino)-butyl]thiazole-1',1'-dioxide
2-(1-methyl-5-nitroimidazol-2-yl)-4-(thiomorpholinoiminomethyl)thiazole-1',1'-dioxide
2-(1-methyl-5-nitroimidazol-2-yl)-4-[1-(thiomorpholinoimino)-ethyl)]thiazole-1',1'-dioxide
2-(1-methyl-5-nitroimidazol-2-yl)-4-(2,6-dimethylthiomorpholinoiminomethyl)thiazole-1',1'-dioxide
2-(1-methyl-5-nitroimidazol-2-yl)-4-(2-methylthiomorpholinoiminomethyl)thiazole-1'-oxide
2-[1-(prop-1-enyl)-5-nitroimidazol-2-yl]-4-[1-(thiomorpholinoimino)ethyl]thiazole-1',1'-dioxide
2-(1-vinyl-5-nitroimidazol-2-yl)-4-(thiomorpholinoiminomethyl)-thiazole
2-(1-vinyl-5-nitroimidazol-2-yl)-4-(thiomorpholinoiminomethyl)-thiazole-1'-oxide
2-(1-methyl-5-nitroimidazol-2-yl)-4-[1-(3-ethylthiomorpholinoimino)ethyl]thiazole-1',1'-dioxide
2-(1-vinyl-5-nitroimidazol-2-yl)-4-(2,3,5,6-tetramethylthiomorpholinoiminomethyl)thiazole
2-(1-methyl-5-nitroimidazol-2-yl)-4-[1-(thiomorpholinoimino)-propyl]thiazole-1',1'-dioxide
2-(1-vinyl-5-nitroimidazol-2-yl)-4-(2-butylthiomorpholinoiminomethyl)thiazole
2-(1-vinyl-5-nitroimidazol-2-yl)-4-(thiomorpholinoiminomethyl)-thiazole-1',1'-dioxide
2-(1-vinyl-5-nitroimidazol-2-yl)-4-(3-methylthiomorpholinoiminomethyl)thiazole-1',1'-dioxide.

As stated above, the compounds of this invention possess anti-parasitic activity. More particularly, the compounds of formula I are active in vivo against several species of Trypanosomidae and display especially powerful action against T. cruzi which is the causative agent of Chagas' disease in humans. To illustrate the potency of the compounds of this invention, the Table below shows the activity of one of the compounds of formula I, i.e. 2-(1-methyl-5-nitroimidazol-2-yl)-4-(thiomorpholinoiminomethyl)-thiazole-1',1'-dioxide (Compound A), compared with that of Nifurtimox, which is a drug known to be effective against T. cruzi and currently sold in South America for the treatment of Chagas' disease. Nifurtimox is 4-[(5-nitrofurfurylident)amino]-3-methylthiomorpholine 1,1-dioxide.

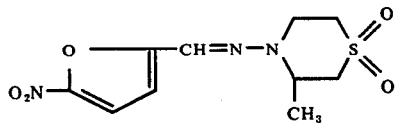

See "WHO Chronicle" (World Health Organization, Geneva, 1969), April 1969, page 194, and also U.S. Pat. No. 3,262,930, especially the fourth entry in Table I and claim 3.

The tests comparing the claimed compounds with Nifurtimox were carried out in mice infected with various strains of *T. cruzi* and the results are expressed in terms of the percentage survival of the mice 60 days after being infected. The drugs were dosed once daily for 10 days except against BH strain where the dosage regime was once daily for 5 days.

Table

| Administration Route | Dose mg/Kg. | Compound A | | | Nifurtimox | | |
|---|---|---|---|---|---|---|---|
| | | BH | Peru | BHC/10 | BH | Peru | BHC/10 |
| i.p. | 12.5 | 100% | 100% | 64% | 82% | 100% | 10% |
| | 6.25 | 40% | 100% | 19% | 0 | 15% | 0 |
| p.o. | 25.0 | 100% | 100% | — | 100% | 100% | 15% |
| | 12.5 | 83% | 100% | 100% | 0 | 100% | 13% |
| | 6.25 | 40% | 80% | 10% | 0 | 0 | 0 |

The BH strain of *T. cruzi* gives a fairly high blood parasitaemia, and low tissue parasitaemia, the Peru strain gives moderate blood and tissue parasitaemia, whilst the BHC/10 strain gives low blood and high tissue parasitaemia. Mice infected with these strains normally die within 12 to 20 days after being infected.

It can be seen from the above results that, whilst Compound A and Nifurtimox are both active against the Peru strain, Compound A retains its effectiveness at lower doses both by the i.p. and p.o. routes. A similar result is obtained against BH strain except that Compound A displays an even greater superiority by the p.o. route. However, it is against BHC/10 strain that the potency of Compound A is most marked since, whilst Nifurtimox is inactive i.p. and orally, Compound A is active at doses as low as 12.5 mg/Kg. Since the existence of *T. cruzi* in the tissues after treatment is believed to be responsible for recurrence of the disease, it will be apparent that the excellent activity of Compound A against the BHC/10 strain (which gives high tissue parasitaemia) makes it potentially very useful in the treatment of Trypanosomiasis and particularly Chagas' disease.

Accordingly, the present invention provides a method of treating parasitic infections which comprises administering an effective dose of a compound of formula I above. The size of the dose and the frequency and duration of treatment will vary depending on such conditions as the route of administration, the severity of the infection, the species of parasite involved and the body weight and general health of the host. However, an effective dosage regime is likely to involve administration of from 1 to b 250 mg/Kg, preferably 5 to 100 mg/Kg, per day for at least 3 days.

The compounds of formula I will normally be used in the form of a pharmaceutical composition comprising the active compound in association with a pharmacologically acceptable diluent or carrier therefor, and such compositions form a part of this invention. Preferably the composition is in the form of a tablet, capsule or other dosage unit form for oral administration, said dosage unit forms normally containing from 5 to 500 mg., preferably 25 to 250 mg., of active ingredient. Alternatively, the composition may be in the form of a solution or suspension for parenteral administration.

In accordance with a further feature of the present invention, there is provided a process for preparing the compounds of formula I which comprises reacting a compound of the formula:

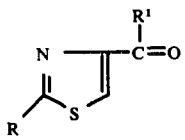

wherein R and R¹ are as defined above, with a compound of the formula:

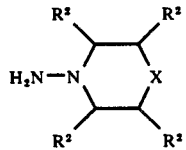

wherein R² and X are as defined above. The reaction is normally carried out in a suitable reaction solvent such as chloroform or dioxan, and at elevated temperatures, conveniently at the reflux temperature of the reaction mixture.

The compounds of formula II are novel and form a part of this invention. Compounds of formula II in which R¹ is hydrogen are preferred. They may be prepared by a number of routes starting from known or readily obtainable 1-(R³-substituted)-2-cyano-5-nitroimidazoles, as shown in the following reaction sequences:

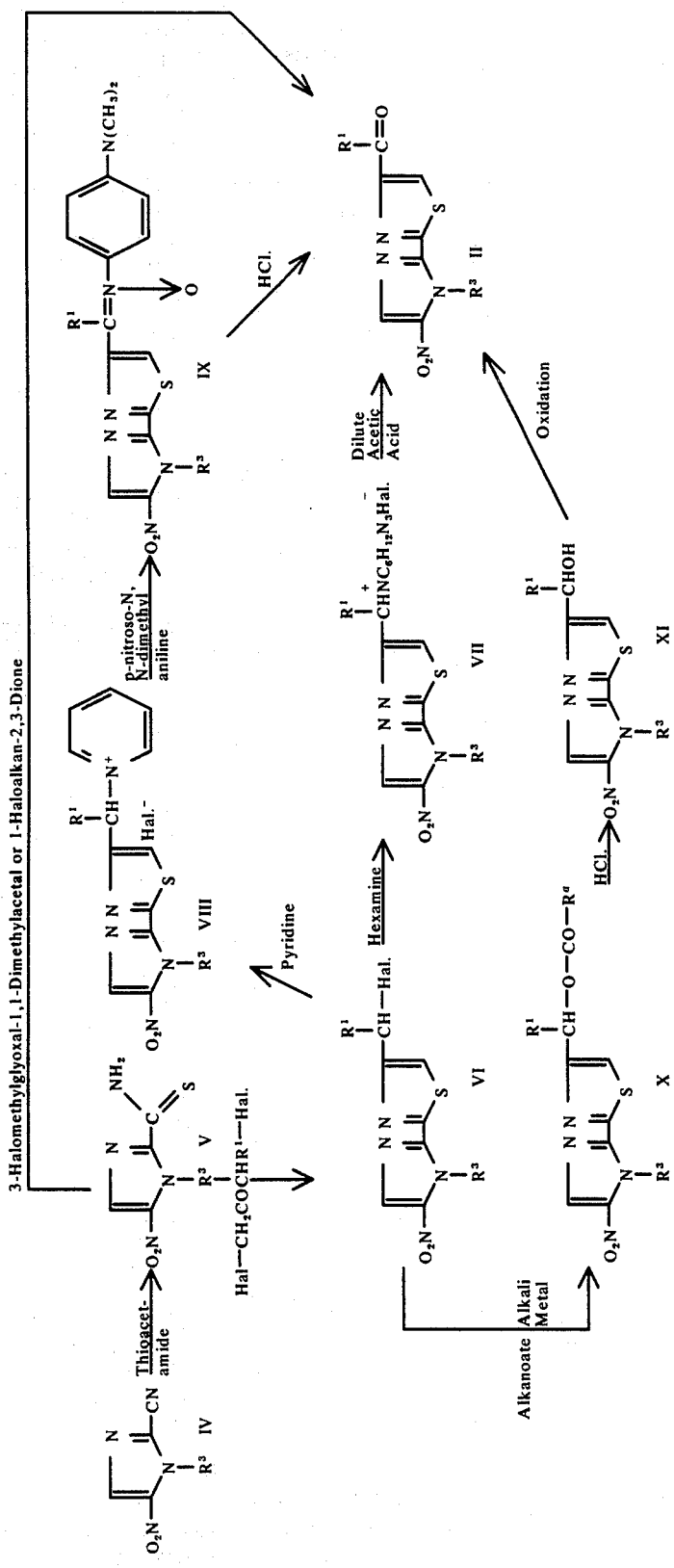

In the foregoing reaction schemes, Hal- represents halogen preferably chlorine or bromine and $R^a$ represents $C_{1-4}$ alkyl. In addition it should be noted that, where a compound of formula I in which $R^3$ is alkenyl is desired, it may be desirable to generate the alkenyl group at a convenient stage after the formation of the thiazole ring, for example by treatment with a strong acid or base respectively, of a corresponding compound in which $R^3$ is a sulphonyloxyalkyl group. The latter compound is prepared in the same procedures beginning with a compound of formula IV wherein the $R^3$ group is, instead, a sulphonyloxyalkyl group.

The conversion of compound IV to compound V is accomplished by reaction with thioacetamide, preferably in a reaction medium comprising a dimethylformamide — hydrogen chloride complex. Preferred reaction temperature is between 45° and 60° C. and the reaction is normally continued for about 6 hours.

Compound V may be converted to a compound of formula II by reaction with a 3-halomethylglyoxal-1,1-dimethylacetal (forming a compound in which $R^1$ is hydrogen) or with a 1-haloalkan-2,3-dione (forming a compound in which $R^1$ is alkyl). For example in the latter case reaction with 1-bromobutan-2,3-dione yields a compound of formula II in which $R^1$ is methyl. This condensation is normally carried out in a suitable solvent such as dioxan and with gentle heating. This method is preferred in the preparation of compounds in which $R^1$ is alkyl.

Compound V may also be converted to Compound VI by reaction with a 1,3-dihaloalkylketone in a suitable solvent such as dimethylformamide or dioxan at elevated temperatures for about 2 to 3 hours. For example reaction with 1,3-dichloroacetone produces a 4-chloromethyl compound of formula VI. Compound VI may then be treated in a number of ways to produce the desired compound of formula II. In one method, compound VI is reacted with an alkali metal salt of an alkanoic acid, for example sodium or potassium acetate, the resultant ester (compound X) hydrolysed in the presence of a mineral acid to yield the alcohol (compound XI) which is oxidised — using a suitable oxidising agent such as manganese dioxide, sodium dichromate in glacial acetic acid or chromium trioxide in sulphuric acid — to yield the compound of formula II. The esterification step is preferably carried out in dimethylformamide at a temperature of about 70° to 95° C.

In another method, compound VI may be reacted with hexamine or pyridine to yield the quaternary compounds VII and VIII respectively. Compound VII on treatment for example with dilute acetic acid yields the desired compound of formula II, this reaction being a specific form of the so-called Sommelet reaction described in Organic Reactions, Volume 8, page 203 (1954). Compound VIII is converted to a compound of formula II by reaction with p-nitroso dimethylaniline in the presence of an alkali metal alkoxide, followed by acid hydrolysis of the resultant nitrone, this reaction sequence being a form of the so-called Krohnke method described in Angewandte Chemie (International Edition), Volume 2 at pages 380–393.

All of compound V to XI are believed to be novel and also form a part of this invention.

The following Examples illustrate the preparation of the above novel intermediates and the production therefrom of the compounds of formula I:

EXAMPLE 1

Dry HCl gas was passed into 750 ml. of dry dimethylformamide with cooling until the exothermic reaction ceased.

1-methyl-5-nitro-2-cyanoimidazole (0.6mole) was dissolved in this mixture at 40° C. Thioacetamide (1.2 mole) was added and stirring continued for 3 hours at 40° C. The resultant solution was poured on to 4 liters of ice/water mixture and stirred for 30 minutes. The precipitate was collected, slurried with water, filtered and dried to yield 1-methyl-2-thiocarbamyl-5-nitroimidazole, m.p. 148°–50° C.

Similarly by using 1-p-toluenesulphonyloxy-5-nitro-2-cyanoimidazole (prepared from the 1-hydroxyethyl compound and p-toluenesulphonyl chloride), there was obtained 1-p-toluenesulphonyloxyethyl-2-thiocarbamyl-5-nitroimidazole.

EXAMPLE 2

The 2-thiocarbamyl compounds from Example 1 (0.1 mole) and 1-bromobutan-2,3-dione (0.20 mole) were dissolved in dioxan (150 ml.) and the solution stirred and heated at 50°–60° C. for 10 minutes. The solution was diluted with water and the precipitate collected and dried. The product was extracted with boiling benzene, the solution filtered and the filtrate decolourised with charcoal. On evaporation of the filtrate, crystallization began and was completed by the addition of petroleum ether. The resulting products were 2-(1-methyl-5-nitroimidazol-2-yl)-4-acetylthiazole and 2-(1-p-toluenesulphonyloxy-5-nitroimidazol-2-vl)-4-acetylthiazole.

Similarly, by reaction of the 1-methyl-2-thiocarbamyl compound with 1-bromopentan-2,3-dione, there was obtained 2-(1-methyl-5-nitroimidazol-2-yl)-4-propionylthiazole, whilst reaction with 3-bromomethylglyoxal-1,1-dimethylacetal followed by acid hydrolysis yielded 2-(1-methyl-5-nitroimidazol-2-yl) thiazole-4-carboxaldehyde.

The resultant 1-p-toluenesulphonyloxy compound (0.054 mole) in ethanol (300 ml.) was stirred with a solution of sodium (0.054 g. atom) in ethanol (45 ml.) at 70° C. Stirring was continued for 30 minutes and, after cooling and standing overnight at room temperature, the resultant precipitate was collected and washed in water to yield 2-(1-vinyl-5-nitroimidazol-2-yl)-4-acetylthiazole.

EXAMPLE 3

The 2-thiocarbamyl compounds from Example 1 (0.27 mole) and 1,3-dichloroacetone (0.55 mole) in dioxan (55 ml.) were stirred and heated at 130° C. for 2 hours. The mixture was poured into water, the resultant precipitate washed with hot water and dried to yield 2-(1-methyl-5-nitroimidazol-2-yl)-4-chloromethylthiazole m.p. 160°–2° C. and 2-(1-p-toluenesulphonyloxyethyl)-5-nitroimidazol-2-yl)-4-chloromethylthiazole respectively. The 1-p-toluenesulphonyloxy compound, on treatment as described at the end of Example 2, yielded 2-(1-vinyl-5-nitroimidazol-2-yl)-4-chloromethylthiazole.

EXAMPLE 4

2-(1-methyl-5-nitroimidazol-2-yl)-4-chloromethylthiazole (0.2 mole) and hexamine (0.3 mole) in chloroform (400 ml.) were stirred and boiled under reflux for 20 hours. The solid product was collected, washed in chloroform and dried to yield 2-(1-methyl-5-nitroimidazol-2-yl)-4-thiazolylmethyl hexaminium chloride. The latter (0.078 mole) was dissolved in water (150 ml.) and glacial acetic acid (150 ml.). Hexamine (10 g.) was added and the solution refluxed for 1½ hours. The solution was evaporated to 50 ml. and water (200 ml.) added. The precipitate was collected and dried to give 2-(1-methyl-5-nitro-imidazol-2-yl)thiazole-4-carboxaldehyde, m.p. 180°–182° C.

EXAMPLE 5

2-(1-Methyl-5-nitroimidazol-2-yl)-4-chloromethylthiazole (0.7 mole) and anhydrous sodium acetate (2.5 mole) were mixed with dimethylformamide and heated for 3½ hours. The reaction mixture was poured on to 2½ liters of ice/water slurry and stirred. The product was collected, washed in water, dried dissolved in boiling benzene and filtered. The filtrate was evaporated to dryness to give 2-(1-methyl-5-nitroimidazol-2-yl)-4-acetoxymethylthiazole.

The latter (0.56 mole) was dissolved in dioxan (700 ml.) and a mixture of concentrated hydrochloric acid (100 ml.) and water (100 l ml.) was added. The mixture was boiled for 45 minutes and then evaporated to about 150 ml. One liter of cold water was added and the resultant product was collected, washed with water and dried to yield 2-(1-methyl-5-nitroimidazol-2-yl)-4-thiazolyl methanol.

To a solution of the latter (0.4 mole) in glacial acetic acid (500 ml.) was added dropwise a solution of sodium dichromate dihydrate (0.14 mole) in glacial acetic acid (100 ml.). The mixture was stirred at 60° C. for 1 hour and the solution poured on to 3 liters of ice/water. The solid precipitate was collected, washed with water, dried, extracted with boiling benzene and the extracts treated with charcoal, filtered and evaporated to yield 2-(1-methyl-5-nitroimidazol-2-yl)thiazole-4-carboxaldehyde.

EXAMPLE 6

By the methods of Examples 4 or 5, the following compounds of formula II were also prepared:

2-(1-vinyl-5-nitroimidazol-2-yl)thiazole-4-carboxaldehyde.

EXAMPLE 7

2-(1-Methyl-5-nitroimidazol-2-yl)thiazole-4-carboxaldehyde (0.02 mole) and N. aminothiomorpholino — 1,1-dioxide (0.022 mole) in chloroform (150 c.c.) were refluxed for 2 hours. After removal of the solvent in vacuo, the resultant orange solid was recrystallized from dimethylformamide to give 2-(1-methyl-5-nitroimidazol-2-yl)-4-(thiomorpholinoiminomethyl)-thiazole-1′,1′-dioxide, m.p. 235°–7° C.

EXAMPLE 8

Using the procedure of Example 7 but reacting N-aminothiomorpholine, N-amino-3-methylthiomorpholine, N-amino-2,6-dimethylthiomorpholine or their 1-oxides or 1,1-dioxides, with the other ketones and aldehydes prepared in Examples 2 and 4 to 6, there were prepared 2-(1-methyl-5-nitroimidazol-2-yl)-4-(thiomorpholinoiminomethyl)thiazole
2-(1-methyl-5-nitroimidazol-2-yl)-4-(thiomorpholinoiminomethyl)thiazole-1-oxide
2-(1-methyl-5-nitroimidazol-2-yl)-4-[(2,6-dimethylthiomorpholinoimino)methyl]thiazole-1′,1′-dioxide
2-(1-methyl-5-nitroimidazol-2-yl)-4-[(3-methylthiomorpholinoimino)methyl]thiazole-1′,1′-dioxide, m.p. 269°–270° C.
2-(1-methyl-5-nitroimidazol-2-yl)-4-[1-(thiomorpholinoimino)ethyl]thiazole-1′,1′-dioxide
2-(1-vinyl-5-nitroimidazol-2-yl)-4-(thiomorpholinoiminomethyl)thiazole
2-(1-vinyl-5-nitroimidazol-2-yl)-4-(thiomorpholinoiminomethyl)thiazole-1′,1′-dioxide
2-(1-methyl-5-nitroimidazol-2-yl)-4-[1-(thiomorpholinoimino)propyl]thiazole
2-(1-methyl-5-nitroimidazol-2-yl)-4-[1-(thiomorpholinoimino)propyl]thiazole-1′,1′-dioxide

We claim:
1. Compound of the formula:

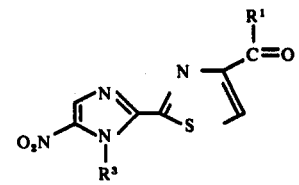

wherein $R^1$ represents hydrogen or $C_{1-4}$ alkyl and $R^3$ represents $C_{1-4}$ alkyl or $C_{2-4}$ alk-l-enyl.
2. Compound according to claim 1, wherein $R^1$ is hydrogen, methyl or ethyl, and $R^3$ represents methyl, ethyl, or vinyl.
3. Compound according to claim 1, wherein $R^1$ is hydrogen or methyl and $R^3$ is methyl or vinyl.
4. Compound according to claim 1, said compound being 2-(1-methyl- or 1-vinyl-5-nitroimidazol-2-yl)thiazole-4-carboxaldehyde.
5. Compound according to claim 1, said compound being 2-(1-methyl- or 1-vinyl-5-nitroimidazol-2-yl)-4-acetylthiazole.
6. Compound according to claim 1 wherein $R^1$ is hydrogen.

* * * * *